US012674806B2

(12) United States Patent
Lipscombe et al.

(10) Patent No.: US 12,674,806 B2
(45) Date of Patent: Jul. 7, 2026

(54) ENDOMETRIOSIS BIOMARKERS

(71) Applicant: Proteomics International Pty Ltd,
West Perth (AU)

(72) Inventors: Richard Lipscombe, Floreat (AU);
Scott Bringans, Harrisdale (AU);
Tammy Casey, Mount Pleasant (AU)

(73) Assignee: Proteomics International (IP) Pty Ltd,
West Perth (AU)

( * ) Notice: Subject to any disclaimer, the term of this
patent is extended or adjusted under 35
U.S.C. 154(b) by 850 days.

(21) Appl. No.: 17/908,883

(22) PCT Filed: Mar. 16, 2021

(86) PCT No.: PCT/AU2021/050227
§ 371 (c)(1),
(2) Date: Sep. 1, 2022

(87) PCT Pub. No.: WO2021/184060
PCT Pub. Date: Sep. 23, 2021

(65) Prior Publication Data
US 2023/0089507 A1     Mar. 23, 2023

(30) Foreign Application Priority Data

Mar. 16, 2020     (AU) ................................. 2020900805

(51) Int. Cl.
*G01N 33/68*          (2006.01)
(52) U.S. Cl.
CPC ..... *G01N 33/6893* (2013.01); *G01N 33/6848*
(2013.01); *G01N 2800/364* (2013.01)

(58) Field of Classification Search
CPC ........... G01N 33/6893; G01N 33/6848; G01N
2800/364; G01N 33/689
USPC ..................................................... 436/86, 43
See application file for complete search history.

(56) References Cited

U.S. PATENT DOCUMENTS

2022/0221472 A1     7/2022 Kobayashi

FOREIGN PATENT DOCUMENTS

WO          2019084682          5/2019
WO          2020218465          10/2020

OTHER PUBLICATIONS

Sun, W.S., et al.,Coexpression of growth arrest-specific gene 6 and
receptor tyrosine kinases, Axl and Sky, in human uterine endome-
trium and ovarian endometriosis, Molecular Human Reproduction,
vol. 8, Issue 6, Jun. 2002, pp. 552-558, https://doi.org/10.1093/
molehr/8.6.552 (Year: 2002).*

(Continued)

*Primary Examiner* — Christine T Mui
(74) *Attorney, Agent, or Firm* — Suzannah K. Sundby,
Esq.; Canady + Lortz LLP

(57)          ABSTRACT

A method comprising the steps of: (a) assessing an expres-
sion level of at least one protein, selected from Table 1, 2 or
3 in a sample from a subject, where in the at least one protein
may be selected from the list comprising: Beta-Ala-His
dipeptidase, Apolipoprotein L1, Methanethiol oxidase, Vita-
min K-dependent protein S, von Willebrand factor, Plasmi-
nogen, Selenoprotein P, Protein disulfide-isomerase A6 and
Inter-alpha-trypsin inhibitor heavy chain H3, and (b) using
the expression level to determine whether the subject has
endometriosis.

15 Claims, 1 Drawing Sheet

(56) References Cited

OTHER PUBLICATIONS

Manfioletti, The Protein Encoded by a Growth Arrest-Specific Gene (gas6) Is a New Member of the VitaminK-Dependent Proteins Related to Protein S, a Negative Coregulator in the Blood Coagulatin Cascade, Molecular and Cellular Biology, Aug. 1993 (Year: 1993).*

Pretta, Atherosclerosis in women with endometriosis, European Journal of Obstetrics & Gynecology and Reproductive Biology 132 (2007) 226-231 (Year: 2007).*

Lee, Limited value of pro-inflammatory oxylipins and cytokines as circulating biomarkers in endometriosis—a targeted 'omics study, Nature, May 19, 2016, 6:26117 (Year: 2016).*

Yang, A Mass Spectrometric Insight Into the Origins of Benign Gynological Disorders, Mass Spectrometry Reviews, 2017, 36, 450-470 (Year: 2017).*

Recarte-Pelz, Arthritis Research & Therapy, 2013, 15:R41 (Year: 2013).*

Extended European Search Report and Written Opinion received in EP21770607 mailed Jul. 1, 2024.

Long et al., Evaluation of novel serum biomarkers and the proteomic differences of endometriosis and adenomyosis using MALDI-TOF-MS, Jul. 1, 2013, pp. 201-205, vol. 288, No. 1, Publisher: Arch Gynecol Obstet.

Uegaki et al., Inhibitor of apoptosis proteins (IAPs) may be effective therapeutic targets for treating endometriosis, Jan. 1, 2015, pp. 149-158, vol. 30, No. 1, Publisher: Hum Reprod.

Xiaoyu et al., Comparative serum proteomic analysis of adenomyosis using the isobaric tags for relative and absolute quantitation technique, Aug. 1, 2013, pp. 505-510, vol. 100, No. 2, Publisher: Fertil Steril.

International Search Report received in PCT/AU2021/050227 mailed Jun. 30, 2021.

Written Opinion received in PCT/AU2021/050227 mailed Jun. 30, 2021.

Anastasiu et al., Biomarkers for the Noninvasive Diagnosis of Endometriosis: State of the Art and Future Perspectives, Mar. 4, 2020, p. 1750, vol. 21, No. 5, Publisher: Int J Mol Sci.

Dutta et al., Investigation of serum proteome alterations in human endometriosis, Jan. 30, 2015, pp. 182-196 (Abstract), vol. 114, Publisher: J Proteomics.

Grande et al., Cervical mucus proteome in endometriosis, Feb. 2, 2017, p. 7, vol. 14, Publisher: Clin Proteomics.

Hwang et al., Identification of biomarkers for endometriosis in plasma from patients with endometriosis using a proteomics approach, Aug. 1, 2014, pp. 725-730, vol. 10, No. 2, Publisher: Mol Med Rep.

Sahar et al., Differential expression of Lumican, Mimecan, Annexin A5 and Serotransferrin in ectopic and matched eutopic endometrium in ovarian endometriosis: a cas, Jan. 1, 2021, pp. 56-60 (Abstract), vol. 37, No. 1, Publisher: Gynecol Endocrinol.

Tamaresis et al., Molecular classification of endometriosis and disease stage using high-dimensional genomic data, Dec. 1, 2014, pp. 4986-4999, vol. 155, No. 12, Publisher: Endocrinology.

Van et al., Identification of novel antigens in blood vessels in rectovaginal endometriosis, Dec. 1, 2007, pp. 875-886, vol. 13, No. 12, Publisher: Mol Hum Reprod.

Yao et al., Deciphering biomarkers of endometriosis by proteomic analysis of eutopic endometrium in infertile patients, May 1, 2021, p. 102043 (Abstract), vol. 50, No. 5, Publisher: J Gynecol Obstet Hum Reprod.

* cited by examiner

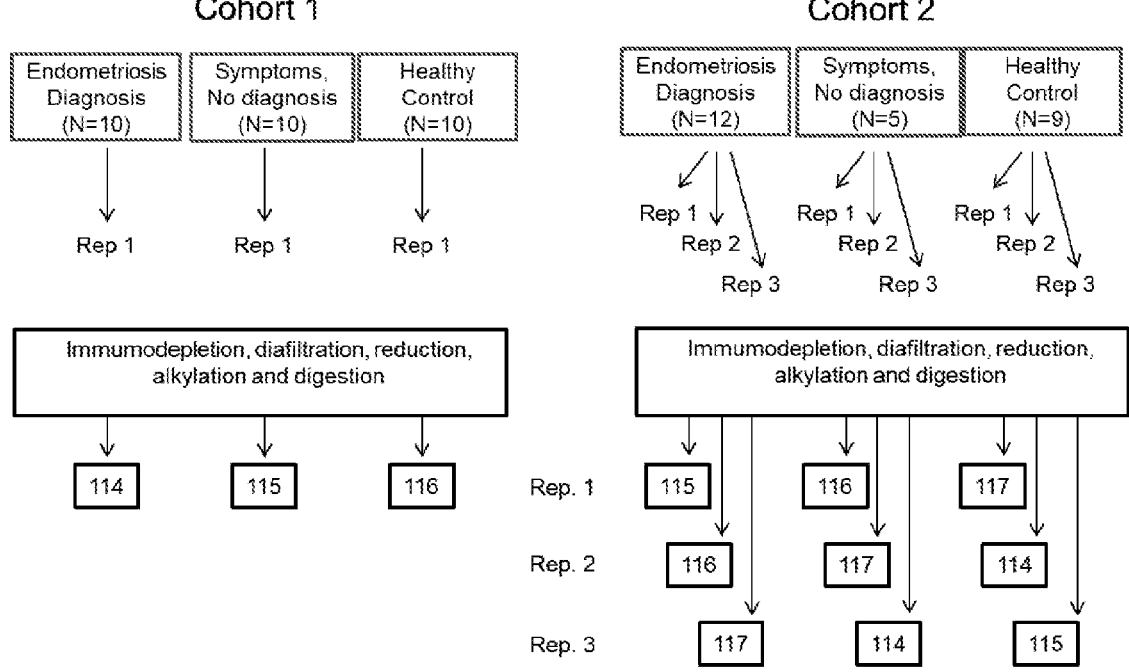

ENDOMETRIOSIS BIOMARKERS

FIELD OF THE INVENTION

The invention relates to biomarkers associated with endometriosis. The invention also relates to screening, diagnostic and prognostic methods of using the biomarkers. Still further the invention relates to methods of assessing medical interventions for endometriosis and methods of identifying drug targets for endometriosis.

BACKGROUND TO THE INVENTION

Endometriosis occurs when the tissues that line the uterus spread outside of the uterine cavity and surround other organs, including in the peritoneum, ovaries, fallopian tubes, pleura and lungs. The condition affects one in ten women in their reproductive years and its incidence and health burden are comparable with diabetes.

Endometriosis causes chronic pain and infertility but is often difficult to diagnose because the symptoms are shared by many other gynaecological conditions. On average, it takes 8.5 years for women to be diagnosed from their first symptoms. Imaging scans and existing blood tests are inconclusive, so the current gold standard for diagnosis is by direct visualisation of the tissue with confirmation by histological analysis. This can only be achieved by invasive laparoscopy/laparotomy under a general anaesthetic, where a camera is inserted into the pelvis through a small cut in the abdominal wall.

With the above in mind there is a need for improved endometriosis biomarkers and associated methods of their use including methods for diagnosing endometriosis.

SUMMARY OF THE INVENTION

The present invention provides a method comprising the steps of:
- (a) assessing an expression level of at least one protein, selected from Table 1, 2 or 3 in a sample from a subject, and
- (b) using the expression level to determine whether the subject has endometriosis.

The present invention also provides a test comprising:
- (a) means for obtaining an expression level of at least one protein selected from Tables 1, 2 or 3 in a sample from a subject; and
- (b) means for processing the expression level generated in step (a) to determine whether the subject has endometriosis.

The present invention also provides for the use of at least one protein, selected from Tables 1, 2 or 3 as a biomarker for endometriosis.

The present invention also provides a method of assessing an endometriosis intervention in a subject, the method comprising the steps of:
- (a) applying the intervention to the subject;
- (b) assessing an expression level of at least one protein selected from Tables 1, 2 or 3 in a sample from the subject; and
- (c) using the expression level to determine the effect of the intervention on the subject.

The present invention also provides for the use of at least one protein selected from Tables 1, 2 or 3 as a target for a therapeutic agent for endometriosis.

BRIEF DESCRIPTION OF DRAWINGS

The following Detailed Description of the Invention, given by way of example, but not intended to limit the invention to specific embodiments described, may be understood in conjunction with the accompanying Figure, in which:

FIG. 1 outlines the study design for biomarkers of endometriosis (Note: the isobaric Tags for Relative and Absolute Quantitation (iTRAQ® labels) are designated 114, 115, 116, 117).

DETAILED DESCRIPTION OF THE INVENTION

According to a first aspect, the present invention provides a method comprising the steps of:
- (a) assessing an expression level of at least one protein, selected from Table 1, 2 or 3, in a sample from a subject, and
- (b) using the expression level to determine whether the subject has endometriosis.

TABLE 1

| ID No. | Protein | Accession number (UniProt) |
|---|---|---|
| 14 | Complement factor H-related protein 2 | P36980 |
| 7 | Beta-Ala-His dipeptidase | Q96KN2 |
| 28 | Sex hormone-binding globulin | P04278 |
| 15 | Corticosteroid-binding globulin | P08185 |
| 5 | Apolipoprotein L1 | O14791 |
| 12 | Catalase | P04040 |
| 9 | C4b-binding protein alpha chain | P04003 |
| 11 | Carbonic anhydrase 2 | P00918 |
| 29 | Superoxide dismutase [Cu-Zn] | P00441 |
| 24 | Peroxiredoxin-1 | Q06830 |
| 2 | Annexin A1 | P04083 |
| 23 | Methanethiol oxidase | Q13228 |
| 8 | Bisphosphoglycerate mutase | P07738 |
| 27 | Rho GDP-dissociation inhibitor 2 | P52566 |
| 10 | C4b-binding protein beta chain | P20851 |
| 26 | Protein S100-A8 | P05109 |
| 1 | ADAMTS-like protein 2 | Q86TH1 |
| 30 | Vitamin K-dependent protein S | P07225 |
| 25 | Peroxiredoxin-2 | P32119 |
| 6 | Beta-2-glycoprotein 1 | P02749 |
| 21 | Hepatocyte growth factor activator | Q04756 |
| 3 | Annexin A3 | P12429 |
| 16 | Endoplasmic reticulum chaperone BiP | P11021 |
| 18 | Flavin reductase (NADPH) | P30043 |
| 17 | Fibrillin-1 | P35555 |
| 4 | Annexin A5 | P08758 |
| 42 | Profilin-1 | P07737 |
| 31 | Afamin | P43652 |
| 48 | von Willebrand factor | P04275 |
| 40 | L-lactate dehydrogenase A chain | P00338 |
| 41 | Plasminogen | P00747 |
| 46 | Selenoprotein P | P49908 |
| 44 | Proteoglycan 4 | Q92954 |
| 38 | Hyaluronan-binding protein 2 | Q14520 |
| 43 | Protein disulfide-isomerase A6 | Q15084 |
| 33 | Coactosin-like protein | Q14019 |
| 36 | Complement component C9 | P02748 |
| 35 | Coagulation factor XII | P00748 |
| 39 | Inter-alpha-trypsin inhibitor heavy chain H3 | Q06033 |
| 37 | Heparin cofactor 2 | P05546 |
| 34 | Coagulation factor X | P00742 |
| 32 | Clusterin | P10909 |
| 47 | Thrombospondin-1 | P07996 |
| 45 | Prothrombin | P00734 |

For the purposes of the present invention the term endometriosis includes the pathological growth of ectopic endometrial-like tissue outside of the uterine cavity. Preferably, the term endometriosis comprises one or more of peritoneal superficial endometriosis, ovarian endometriosis and deep infiltrating endometriosis. Deep infiltrating endometriosis may comprise one or more of pathological growth of ectopic endometrial-like tissue in the uterosacral ligaments, rectovaginal space, the upper third of the posterior vaginal wall, the bowel and/or the urinary tract.

Preferably, the at least one protein comprises a plurality of proteins such as two, three, four or five proteins from Table 1.

Preferably, the at least one protein comprises Complement factor H-related protein 2, Beta-Ala-His dipeptidase, Sex hormone-binding globulin, Corticosteroid-binding globulin, Apolipoprotein L1, Catalase, C4b-binding protein alpha chain, Carbonic anhydrase 2, Superoxide dismutase [Cu—Zn], Peroxiredoxin-1, Annexin A1, Methanethiol oxidase, Bisphosphoglycerate mutase, Profilin-1, Afamin, von Willebrand factor, L-lactate dehydrogenase A chain, Plasminogen, Selenoprotein P, Proteoglycan 4, Hyaluronan-binding protein 2, Protein disulfide-isomerase A6 or Coactosin-like protein.

Preferably the at least one protein comprises at least two, three or four of: Complement factor H-related protein 2, Beta-Ala-His dipeptidase, Sex hormone-binding globulin, Corticosteroid-binding globulin, Apolipoprotein L1, Catalase, C4b-binding protein alpha chain, Carbonic anhydrase 2, Superoxide dismutase [Cu—Zn], Peroxiredoxin-1, Annexin A1, Methanethiol oxidase, Bisphosphoglycerate mutase, Profilin-1, Afamin, von Willebrand factor, L-lactate dehydrogenase A chain, Plasminogen, Selenoprotein P, Proteoglycan 4, Hyaluronan-binding protein 2, Protein disulfide-isomerase A6 or Coactosin-like protein.

Preferably, the at least one protein comprises at least one protein selected from Table 2.

TABLE 2

| ID No. | Protein | Accession number |
|---|---|---|
| 7 | Beta-Ala-His dipeptidase | Q96KN2 |
| 5 | Apolipoprotein L1 | O14791 |
| 9 | C4b-binding protein alpha chain | P04003 |
| 23 | Methanethiol oxidase | Q13228 |
| 10 | C4b-binding protein beta chain | P20851 |
| 1 | ADAMTS-like protein 2 | Q86TH1 |
| 30 | Vitamin K-dependent protein S | P07225 |

Even more preferably, the at least one protein comprises two, three, four or five proteins selected from Table 2.

Preferably, the at least one protein comprises at least one protein from Table 2 selected from the list comprising: Beta-Ala-His dipeptidase, Apolipoprotein L1, Methanethiol oxidase and Vitamin K-dependent protein S.

Even more preferably, the at least one protein comprises two, three, four or five proteins from Table 2 selected from the list comprising: Beta-Ala-His dipeptidase, Apolipoprotein L1, Methanethiol oxidase and Vitamin K-dependent protein S.

Preferably, the at least one protein comprises at least one protein selected from Table Table 3

TABLE 3

| ID No. | Protein | Accession number |
|---|---|---|
| 42 | Profilin-1 | P07737 |
| 10 | C4b-binding protein beta chain | P20851 |
| 48 | von Willebrand factor | P04275 |
| 40 | L-lactate dehydrogenase A chain | P00338 |
| 41 | Plasminogen | P00747 |
| 46 | Selenoprotein P | P49908 |
| 38 | Hyaluronan-binding protein 2 | Q14520 |

TABLE 3-continued

| ID No. | Protein | Accession number |
|---|---|---|
| 43 | Protein disulfide-isomerase A6 | Q15084 |
| 33 | Coactosin-like protein | Q14019 |
| 36 | Complement component 9 | P02748 |
| 35 | Coagulation factor XII | P00748 |
| 39 | Inter-alpha-trypsin inhibitor heavy chain H3 | Q06033 |
| 9 | C4b-binding protein alpha chain | P04003 |
| 37 | Heparin cofactor 2 | P05546 |

Even more preferably, the at least one protein comprises two, three, four or five proteins selected from Table 3.

Preferably, the at least one protein comprises at least one protein from Table 3 selected from the list comprising: von Willebrand factor, Plasminogen, Selenoprotein P, Protein disulfide-isomerase A6 and Inter-alpha-trypsin inhibitor heavy chain H3.

Even more preferably, the at least one protein comprises two, three, four or five proteins from Table 3 selected from the list comprising: von Willebrand factor, Plasminogen, Selenoprotein P, Protein disulfide-isomerase A6 and Inter-alpha-trypsin inhibitor heavy chain H3.

According to another preferred form of the invention, the at least one protein comprises at least one protein selected from the list comprising: Beta-Ala-His dipeptidase, Apolipoprotein L1, Methanethiol oxidase, Vitamin K-dependent protein S, von Willebrand factor, Plasminogen, Selenoprotein P, Protein disulfide-isomerase A6 and Inter-alpha-trypsin inhibitor heavy chain H3.

Even more preferably, the at least one protein comprises two, three, four or five proteins selected from the list comprising: Beta-Ala-His dipeptidase, Apolipoprotein L1, Methanethiol oxidase, Vitamin K-dependent protein S, von Willebrand factor, Plasminogen, Selenoprotein P, Protein disulfide-isomerase A6 and Inter-alpha-trypsin inhibitor heavy chain H3.

The step (a) of assessing an expression level of at least one protein can comprise any suitable method for assessing protein expression. Preferably, step (a) comprises at least one of spectrometry such as mass spectrometry, surface enhanced Raman spectroscopy, flow cytometry, ELISA, protein arrays including mass-sensing BioCD protein array, protein micro-arrays, quantum dots based detection, electrochemical immunoassay, gel electrophoresis, 9G DNA technology, nanoparticles including lanthanide chelates such as europium EuNPs and gold nanoparticles, immune-affinity mass spectrometry and immune capture mass spectrometry.

When step (a) comprises mass spectrometry it may comprise multiple reaction monitoring (MRM) mass spectrometry or selective reaction monitoring (SRM) mass spectrometry.

Preferably, step (a) comprises assessing the expression level of the at least one protein by assessing the amount of a fragment or peptide of the at least one protein.

Preferably, step (a) comprises quantifying the expression level of the at least one protein.

Preferably, step (a) comprise quantifying the expression level of the at least one protein relative to the expression level of the at least one protein in a subject without endometriosis.

Step (a) may also comprise labelling the at least one protein. Exemplary labels include protein labels e.g. biotin, active site probes, enzyme conjugates e.g. HRP, and fluorescent probes, isotopic labelling and isobaric labelling.

The sample may comprise a biological sample and/or sub-samples thereof. Preferably, the biological sample is a body fluid such as blood, serum, plasma, urine, sweat, tears, saliva, sputum, or any combination or fraction thereof. Other non-limiting examples of a biological sample include whole blood, peripheral blood, ascites, cerebrospinal fluid, buccal sample, cavity rinse, organ rinse, bone marrow, synovial fluid, aqueous humor, amniotic fluid, cerumen, breast milk, broncheoalveolar lavage fluid, female ejaculate, sweat, faecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, or other lavage fluids. A biological sample can also include the blastocyl cavity, umbilical cord blood, or maternal circulation which can be of foetal or maternal origin. The biological sample can also be a tissue sample or biopsy. Sub-samples include extracts from the sample including protein extracts.

Preferably, the subject is a mammal such as a human. A subject can be one who has been previously diagnosed or identified as having endometriosis, and optionally has already undergone, or is undergoing, a therapeutic intervention. Alternatively, a subject can also be one who has not been previously diagnosed or identified as having endometriosis. For example, a subject can be one who exhibits one or more risk factors for endometriosis, or a subject who does not exhibit any such risk factors or a subject who is asymptomatic for endometriosis. A subject can also be one who is suffering from or at risk of developing endometriosis.

Step (b) comprises any use of the expression level from step (a) to determine whether the subject has endometriosis.

Preferably, the expression level from step (a) alone determines whether the subject has endometriosis. However, the expression level from step (a) may partially determine whether the subject has endometriosis. In this regard, the expression level from step (a) may be combined with a second measure to determine whether the subject has endometriosis.

Preferably, step (b) comprises comparing the expression level from step (a) with a reference value indicative of endometriosis.

Preferably, the reference value is a protein expression level. For example, the reference value may be a reference protein expression level from at least one second subject, wherein the reference protein expression level is known to correlate with endometriosis.

The at least one second subject can be a cohort or population of subjects.

Another use, according to step (b) of the expression level from step (a) is comparing it with another expression level from the same subject taken at a different time. Such use allows for the comparison of expression levels, and hence whether the subject has endometriosis, over time in a subject.

Preferably, the method of the present invention determines whether the subject has endometriosis with a sensitivity of at least about 70%, 75%, 80%, 85%, 90%, 95%, 96%, 97%, 98%, 98%, 99%, 99.5%, or about 100%.

Preferably, the method of the present invention determines whether the subject has endometriosis with a specificity of at least about 70%, 75%, 80%, 85%, 90%, 95%, 96%, 97%, 98%, 98%, 99%, 99.5%, or about 100%.

Preferably, the method of the present invention determines whether the subject has endometriosis with an accuracy of at least about 70%, 75%, 80%, 85%, 90%, 95%, 96%, 97%, 98%, 98%, 99%, 99.5%, or about 100%.

The method may involve the use of a control to better assess the expression level of the at least one protein and use it to determine whether the subject has endometriosis.

Preferably, the control is a control protein such as control protein that is not differentially expressed with respect to endometriosis.

According to a second aspect the present invention provides for the use of at least one protein selected from Tables 1, 2, or 3 to determine whether a subject has endometriosis. The other preferred features of the method described above in relation to the first aspect also form preferred features of this aspect of the invention.

According to a third aspect of the present invention there is provided a test comprising:

(a) means for obtaining an expression level of at least one protein selected from Tables 1, 2 or 3 in a sample from a subject; and (b) means for processing the expression level generated in step (a) to determine whether the subject has endometriosis.

The other preferred features of the method described above in relation to the first aspect also form preferred features of this aspect of the invention. For example, the means for obtaining the expression level may comprise any suitable method for assessing expression of protein.

Preferably the test comprises an apparatus.

Preferably, the apparatus comprises a spectrometer.

Preferably, the test comprises a kit.

Preferably, the kit comprises a reagent for detecting the at least one protein.

Preferably, the kit comprises written instructions for quantifying an expression level of the at least one protein and/or for determining whether a subject has endometriosis based on the expression level. The written instructions may include instructions for comparing protein expression and/or a predetermined value (e.g., a value for determining whether the expression level of a protein is indicative of endometriosis).

Preferably, the kit comprises any one or more of the following: a detectable label, standards, sample buffer(s) and controls (positive and/or negative).

The proteins and combinations thereof of the present invention can be implemented in a range of test systems. Typically, test systems include a means for obtaining test results from a sample, a means for collecting, storing, processing and/or tracking test results for the sample, usually in a database and a means for reporting test results. The means for obtaining test results can include a module adapted for automatic testing utilising one or more of biochemical, immunological and protein detection assays. Some test systems can process multiple samples and can run multiple tests on a given sample. The means for collecting, storing, processing and/or tracking test results may comprise a physical and/or electronic data storage device such as a hard drive or flash memory or paper print-outs. The means for reporting test results can include a visible display, a link to a data structure or database, or a printer. In this regard, the reporting means may simply be a data link that is adapted to send results to another device such as a database, visual display, or printer.

Typically, test results from system of the present invention serve as inputs to a computer or microprocessor programmed with a machine code or software that takes the data relating to the expression level of the at least one protein described herein and determines the risk of developing or already having endometriosis.

The invention provides improved diagnosis and prognosis of endometriosis. The risk of having or developing endometriosis can be assessed by measuring the expression of one or more of the proteins in Tables 1, 2 or 3, and comparing the measured values to reference or index values. Such a comparison can be undertaken with mathematical algorithms or formula in order to combine information from results of multiple individual proteins and other parameters into a single measurement or index. Subjects identified as having an increased risk of endometriosis can optionally be selected to receive treatment regimens, such as administration of prophylactic or therapeutic compounds.

The expression level of the at least one protein can be measured in the sample and compared to a reference or normal level, utilizing techniques such as reference limits, discrimination limits, or risk defining thresholds to define cut-off points and abnormal values for endometriosis. The normal control level is the level of one or more proteins or combined biomarker indices typically found in a subject not suffering from endometriosis. The normal and abnormal levels and cut-off points may vary based on whether the at least one protein is used alone or in a formula combined with other biomarkers into an index. Alternatively, the normal or abnormal level can be a database of biomarker patterns or "signatures" from previously tested subjects who did or did not develop endometriosis over a clinically relevant time horizon.

Thus, the expression levels of the at least one protein can be used to generate a profile or signature of subjects: (i) who do not have and are not expected to develop endometriosis and/or (ii) who have or expected to develop such conditions. The profile of a subject can be compared to a predetermined or reference biomarker profile to diagnose or identify subjects at risk for developing endometriosis, to monitor the progression of the endometriosis, as well as the rate of progression of the endometriosis, and to monitor the effectiveness of interventions. Profiles of the present invention are preferably contained in a machine-readable medium and are "live" insofar as they can be updated with further data that comes to hand, thus improving the strength and clinical significance of the biomarkers. Data concerning the levels of the at least one protein of the present invention can also be combined or correlated with other data or test results, such as, without limitation, measurements of clinical parameters or other algorithms for endometriosis. The machine-readable media can also comprise subject information such as medical history and any relevant family history.

The present invention also provides for the use of at least one protein, selected from Tables 1, 2 or 3 as a biomarker for endometriosis.

The methods of the present invention can also include assessing endometriosis intervention. Thus, according to another aspect the present invention provides a method of assessing an endometriosis intervention in a subject, the method comprising the steps of:

(a) applying the intervention to the subject;

(b) assessing an expression level of at least one protein selected from Tables 1, 2 or 3 in a sample from the subject; and (c) using the expression level to determine the effect of the intervention on the subject.

Preferably, the expression level of the at least one protein is assessed at least twice. In this regard, changes in the expression levels after the intervention may identify the intervention as an intervention for treating endometriosis.

Preferably the expression level of the at least one protein is assessed before, during and/or after the intervention.

Preferably, the intervention is selected from the list comprising: hormone therapy, hormonal contraceptives, androgenic agents Gonadotropin-releasing hormone (Gn-RH) agonists and antagonists, progestin therapy, aromatase inhibitors and surgery including laser surgery.

The present invention also provides for the use of at least one protein selected from Tables 1, 2 or 3 as a target for a therapeutic agent for endometriosis. In this regard, the proteins described herein may be useful as drug targets.

The various aspects of the present invention can provide, for example, a relatively economical, accurate, non-invasive, and easy to implement test for detection of endometriosis. Methods of the present disclosure can aid early detection of endometriosis. Methods of the present disclosure can be useful for subjects with undiagnosed endometriosis. Methods of the present disclosure can reduce the rate of false positives and false negatives obtained from other approaches to assessing endometriosis and can improve the accuracy of diagnosis.

General

Those skilled in the art will appreciate that the invention described herein is susceptible to variations and modifications other than those specifically described. The invention includes all such variation and modifications. The invention also includes all of the steps and features referred to or indicated in the specification, individually or collectively and any and all combinations or any two or more of the steps or features. Each document, reference, patent application or patent cited in this text is expressly incorporated herein in their entirety by reference, which means that it should be read and considered by the reader as part of this text. That the document, reference, patent application or patent cited in this text is not repeated in this text is merely for reasons of conciseness. None of the cited material or the information contained in that material should, however be understood to be common general knowledge.

The present invention is not to be limited in scope by any of the specific embodiments described herein. These embodiments are intended for the purpose of exemplification only. Functionally equivalent products and methods are clearly within the scope of the invention as described herein.

The invention described herein may include one or more range of values (e.g. size etc). A range of values will be understood to include all values within the range, including the values defining the range, and values adjacent to the range which lead to the same or substantially the same outcome as the values immediately adjacent to that value which defines the boundary to the range.

Throughout this specification, unless the context requires otherwise, the word "comprise" or variations such as "comprises" or "comprising", will be understood to imply the inclusion of a stated integer or group of integers but not the exclusion of any other integer or group of integers.

Other definitions for selected terms used herein may be found within the detailed description of the invention and apply throughout. Unless otherwise defined, all technical terms used herein have the same meaning as commonly understood to one of ordinary skill in the art to which the invention belongs.

EXAMPLES

Example 1—Identification of Endometriosis Biomarkers

1. Materials/Methods

Study Demographics

The study was approved by the Belberry Human Research Ethics Committee and all participants gave informed consent. Blood samples from participants were collected in EDTA tubes. Plasma was separated by centrifugation (1000 g, 10 min) within 2 hours of collection and stored at −80° C.

The study was performed on two independent cohorts collected by the Wesley Medical Research Institute. In the first cohort, 30 individuals were divided into 3 groups as follows: an endometriosis group (n=10, endometriosis) where endometriosis had been diagnosed by laparoscopy, a symptoms only group (n=10, no diagnosis) where patients displayed symptoms of endometriosis but laparoscopy did not confirm the diagnosis, and a healthy control group with no pelvic symptoms (n=10, control). In the second cohort, 26 individuals were divided into 3 groups as follows: endometriosis group (n=12), a no diagnosis group (n=5), and a healthy control group (n=9).

Plasma Preparation and Isobaric Tag (iTRAQ®) Labelling

Individual plasma samples were pooled for each group. The first cohort was analysed as a single replicate and the second cohort was analysed as 3 replicates (FIG. 1). Technical replicates of the second cohort were generated by splitting each of the groups into three aliquots (FIG. 1).

Fourteen high-abundant proteins in plasma were immunodepleted using a MARS14 chromatography column (Agilent Technologies) before samples were desalted on Vivaspin® 6 10 kDa centrifugal concentrators (Sartorius). Samples were first reduced, alkylated, and trypsin digested. The resulting sample peptide concentrations were measured and normalised to provide equivalent amounts for labelling with isobaric tags for relative and absolute quantitation (iTRAQ®) reagents (Sciex) according to the manufacturer's instructions. The iTRAQ® 4-plex reagents applications kit enabling simultaneous protein identification and quantitation was used. Samples were labelled according to the scheme in FIG. 1.

Peptides were desalted on a Strata-X™ 33 μm polymeric reversed phase columns (Phenomenex) and dissolved in a buffer containing 2% acetonitrile 0.1% formic acid before separation by high pH on an Agilent 1100 HPLC system using a Zorbax® C18 liquid chromatographic column (2.1× 150 mm). Peptides were eluted with a linear gradient of 20 mM ammonium formate, 2% ACN to 20 mM ammonium formate, 90% ACN at 0.2 ml/min. Ninety five fractions were concatenated into 12 fractions and dried down. Each fraction was analysed by electrospray ionisation mass spectrometry using a Thermo UltiMate 3000 nanoflow UHPLC system (Thermo Scientific) coupled to a Q Exactive HF mass spectrometer (Thermo Scientific). Peptides were loaded onto an Acclaim™ PepMap™ 100 C18 LC Column, 2 μm particle size×150 mm (Thermo Scientific) and separated with a linear gradient of water/acetonitrile/0.1% formic acid (v/v).

Data Analysis

Protein identification and quantification were performed using ProteinPilot™ 5.0 (Sciex). MS/MS spectra were searched against the human SwissProt database. Search parameters were: Sample type: iTRAQ® 4plex (peptide labelled); Cys alkylation: MMTS; Digestion: Trypsin; Instrument: Orbi MS and Orbi MS/MS; Special factors:

None; Species: *Homo sapiens*; Quantitate tab checked; Bias correction and Background correction tabs checked; ID focus: Biological modifications; Search effort: Thorough; Detected protein threshold [Unused ProtScore (Conf)]: 0.05 (10.0%); FDR Analysis tab checked.

All identified proteins had an Unused Protscore of >1.3 (which corresponds to proteins identified with >95% confidence) and a global false discovery rate (FDR) of <0.1% determined at the protein level using the software's PSPEP algorithm. Proteins found to be differentially expressed in either Endometriosis Diagnosis group vs Healthy Control group and/or Endometriosis Diagnosis group vs Symptoms, No Diagnosis group were considered as candidate biomarkers for endometriosis only if they were not differentially expressed in the Symptoms, No Diagnosis group vs Healthy Control group. To clarify, if proteins were differentially expressed between the Symptoms, No Diagnosis group vs Healthy Control group they were not considered as biomarkers for endometriosis.

Primary selection criteria were established and applied where differentially expressed proteins were required to have at least two unique peptides with confidence >95% and have significantly different protein ratios (fold change of >10%) in at least one replicate from both of the cohorts (P value of ≤0.05, as calculated by the software).

Secondary selection criteria were also established and applied to select further biomarkers to widen the pool of potential candidates. To be considered as a secondary candidate a protein needed to fulfill 2 rules across both cohorts. Firstly, one of the two cohort data points must meet the primary selection criteria. The second data point from the other cohort must have either ≥2 fold change in protein abundance with at least 2 high confidence peptides (>95%) or have a P Value of 50.1 with the fold change >10% and with at least 2 high confidence peptides (>95%).

Results

Using two independent cohorts, patients with endometriosis diagnosed by laparoscopy were compared to a) patients with symptoms only, and b) a healthy control group with no pelvic symptoms.

The proteome coverage for each of the four experiments outlined in FIG. 1 is shown in Table A.

TABLE A

| Proteome Coverage (Proteins identified) in four experiments | | | | |
| --- | --- | --- | --- | --- |
| | Cohort 1 Replicate 1 | Cohort 2 Replicate 1 | Cohort 2 Replicate 2 | Cohort 2 Replicate 3 |
| Proteins identified | 744 | 582 | 473 | 623 |

Identifications are at the 95% confidence level.

The selection criteria described in the data analysis section were applied to the protein identification and quantitation output and a list of candidate biomarkers were determined to be significant by comparing protein expression in the Endometriosis Diagnosis versus Healthy Controls and the Endometriosis Diagnosis versus Symptoms, No Diagnosis. Further analysis of these candidate biomarkers involved:

averaging significant fold changes across replicates for each protein;

Significant P values are shown as less than the least significant P value for that protein across the replicates. The number of data points used for the averaging has been included (out of 4 possible replicates).

Biomarkers were then ranked by P value, (and if equal) then Significant data points, (and if equal) then Fold change.

The outcome of this further analysis resulted in the biomarkers set out in the Tables B and C.

The invention claimed is:

1. A method of treating a subject for endometriosis, comprising the steps of:

(a) assessing an expression level of at least one protein, selected from the group consisting of Complement

TABLE B

Endometriosis Diagnosis vs Healthy Controls Ranked Summary Data

| Ref Endo vs Healthy | Accession number | Average Significant Fold Change | Significant P value | # Significant Data Points |
|---|---|---|---|---|
| 14 Complement factor H-related protein 2 | P36980 | −3.6 | <0.004 | 2 |
| 7 Beta-Ala-His dipeptidase | Q96KN2 | 1.7 | <0.002 | 2 |
| 28 Sex hormone-binding globulin | P04278 | 3.2 | <0.01 | 3 |
| 15 Corticosteroid-binding globulin | P08185 | 3.0 | <0.01 | 3 |
| 5 Apolipoprotein L1 | O14791 | 1.9 | <0.01 | 2 |
| 12 Catalase | P04040 | 1.8 | <0.01 | 2 |
| 9 C4b-binding protein alpha chain | P04003 | −4.0 | <0.02 | 3 |
| 19 Haemoglobin subunit alpha | P69905 | 3.2 | <0.02 | 3 |
| 11 Carbonic anhydrase 2 | P00918 | 2.8 | <0.02 | 3 |
| 29 Superoxide dismutase [Cu-Zn] | P00441 | 2.1 | <0.02 | 3 |
| 20 Haemoglobin subunit delta | P02042 | 2.6 | <0.02 | 2 |
| 24 Peroxiredoxin-1 | Q06830 | 2.1 | <0.02 | 2 |
| 2 Annexin A1 | P04083 | 1.9 | <0.02 | 2 |
| 23 Methanethiol oxidase | Q13228 | 1.9 | <0.02 | 2 |
| 8 Bisphosphoglycerate mutase | P07738 | 1.7 | <0.02 | 2 |
| 27 Rho GDP-dissociation inhibitor 2 | P52566 | 2.9 | <0.03 | 2 |
| 10 C4b-binding protein beta chain | P20851 | −2.7 | <0.03 | 2 |
| 26 Protein S100-A8 | P05109 | 2.2 | <0.03 | 2 |
| 30 Vitamin K-dependent protein S | P07225 | −1.6 | <0.03 | 2 |
| 1 ADAMTS-like protein 2 | Q86TH1 | −1.9 | <0.03 | 2 |
| 25 Peroxiredoxin-2 | P32119 | 2.9 | <0.04 | 4 |
| 6 Beta-2-glycoprotein 1 | P02749 | −1.3 | <0.04 | 2 |
| 21 Hepatocyte growth factor activator | Q04756 | −1.8 | <0.04 | 2 |
| 13 Complement component C6 | P13671 | −1.3 | <0.05 | 2 |
| 22 IgGFc-binding protein | Q9Y6R7 | −1.3 | <0.05 | 2 |
| 3 Annexin A3 | P12429 | 2.0 | <0.07 | 2 |
| 16 Endoplasmic reticulum chaperone BiP | P11021 | 1.5 | <0.07 | 2 |
| 18 Flavin reductase (NADPH) | P30043 | 2.2 | <0.08 | 2 |
| 17 Fibrillin-1 | P35555 | −2.1 | <0.08 | 2 |
| 4 Annexin A5 | P08758 | 1.9 | <0.09 | 2 |

TABLE C

Endometriosis Diagnosis vs Symptoms (no Diagnosis) Ranked Summary Data

| Ref Endo vs Symptoms | Accession number | Average Significant Fold Change | Significant P value | # Significant Data Points |
|---|---|---|---|---|
| 42 Profilin-1 | P07737 | 2.1 | <0.003 | 2 |
| 10 C4b-binding protein beta chain | P20851 | −2.0 | <0.003 | 2 |
| 31 Afamin | P43652 | −2.2 | <0.002 | 2 |
| 48 von Willebrand factor | P04275 | 4.2 | <0.001 | 2 |
| 40 L-lactate dehydrogenase A chain | P00338 | 2.1 | <0.001 | 2 |
| 41 Plasminogen | P00747 | −2.1 | <0.001 | 2 |
| 46 Selenoprotein P | P49908 | −1.7 | <0.01 | 2 |
| 44 Proteoglycan 4 | Q92954 | −1.4 | <0.02 | 3 |
| 38 Hyaluronan-binding protein 2 | Q14520 | −3.3 | <0.02 | 2 |
| 43 Protein disulfide-isomerase A6 | Q15084 | 2.8 | <0.02 | 2 |
| 33 Coactosin-like protein | Q14019 | 2.4 | <0.02 | 2 |
| 36 Complement component C9 | P02748 | −2.7 | <0.03 | 4 |
| 35 Coagulation factor XII | P00748 | −2.4 | <0.03 | 4 |
| 39 Inter-alpha-trypsin inhibitor heavy chain H3 | Q06033 | −2.1 | <0.03 | 3 |
| 9 C4b-binding protein alpha chain | P04003 | −2.2 | <0.05 | 4 |
| 37 Heparin cofactor 2 | P05546 | −1.6 | <0.05 | 3 |
| 26 Protein S100-A8 | P05109 | 1.7 | <0.05 | 2 |
| 34 Coagulation factor X | P00742 | −1.2 | <0.06 | 2 |
| 32 Clusterin | P10909 | −2.4 | <0.07 | 3 |
| 47 Thrombospondin-1 | P07996 | −1.4 | <0.08 | 4 |
| 45 Prothrombin | P00734 | −1.4 | <0.08 | 2 | factor H-related protein 2, Beta-Ala-His dipeptidase, Sex hormone-binding globulin, Corticosteroid-binding globulin, Apolipoprotein L1, Catalase, C4b-binding protein alpha chain, Carbonic anhydrase 2, Superoxide dismutase [Cu—Zn], Peroxiredoxin-1, Annexin A1, Methanethiol oxidase, Bisphosphoglycerate mutase, Rho GDP-dissociation inhibitor 2, C4b-binding protein beta chain, Protein S100-A8, ADAMTS-like protein 2, Vitamin K-dependent protein S, Peroxiredoxin-2, Beta-2-glycoprotein 1, Hepatocyte growth factor activator, Annexin A3, Endoplasmic reticulum chaperone BiP, Flavin reductase (NADPH), Fibrillin-1, Annexin A5, Profilin-1, Afamin, von Willebrand factor, L-lactate dehydrogenase A chain, Plasminogen, Selenoprotein P, Proteoglycan 4, Hyaluronan-binding protein 2, Protein disulfide-isomerase A6, Coactosin-like protein, Complement component C9, Coagulation factor XII, Inter-alpha-trypsin inhibitor heavy chain H3, Heparin cofactor 2, Coagulation factor X, Clusterin, Thrombospondin-1, and Prothrombin, wherein said at least one protein comprises Vitamin K-dependent protein S, in a sample from the subject, (b) determining that the subject has endometriosis based on the expression level; and (c) administering to the subject an endometriosis treatment selected from hormone therapy, hormonal contraceptives, androgenic agents, Gonadotropin-releasing hormone (Gn-RH) agonists and antagonists, progestin therapy, aromatase inhibitors, and surgery.

2. The method according to claim 1, wherein the at least one protein further comprises one or more proteins selected from the list consisting of: Beta-Ala-His dipeptidase, Apolipoprotein L1, Methanethiol oxidase, von Willebrand factor, Plasminogen, Selenoprotein P, Protein disulfide-isomerase A6, Inter-alpha-trypsin inhibitor heavy chain H3, L-lactate dehydrogenase A chain, Beta-2-glycoprotein 1, Afamin, Clusterin, Prothrombin, Hepatocyte growth factor activator, Endoplasmic reticulum chaperone BiP, Peroxiredoxin-2, Coagulation factor XII, Complement component C9, Complement factor H related protein 2, Heparin cofactor 2, and C4b binding protein alpha chain.

3. The method according to claim 1, wherein the at least one protein comprises two, three, four or five proteins.

4. The method according to claim 1, wherein the at least one protein further comprises at least two proteins selected from the list consisting of: Beta-Ala-His dipeptidase, Apolipoprotein L1, Methanethiol oxidase, von Willebrand factor, Plasminogen, Selenoprotein P, Protein disulfide-isomerase A6, Inter-alpha-trypsin inhibitor heavy chain H3, L-lactate dehydrogenase A chain, Beta-2-glycoprotein 1, Afamin, Clusterin, Prothrombin, Hepatocyte growth factor activator, Endoplasmic reticulum chaperone BiP, Peroxiredoxin-2, Coagulation factor XII, Complement component C9, Complement factor H related protein 2, Heparin cofactor 2, and C4b binding protein alpha chain.

5. The method according to claim 1, wherein the at least one protein further comprises at least three proteins selected from the list consisting of: Beta-Ala-His dipeptidase, Apolipoprotein L1, Methanethiol oxidase, von Willebrand factor, Plasminogen, Selenoprotein P, Protein disulfide-isomerase A6, Inter-alpha-trypsin inhibitor heavy chain H3, L-lactate dehydrogenase A chain, Beta-2-glycoprotein 1, Afamin, Clusterin, Prothrombin, Hepatocyte growth factor activator, Endoplasmic reticulum chaperone BiP, Peroxiredoxin-2, Coagulation factor XII, Complement component C9, Complement factor H related protein 2, Heparin cofactor 2, and C4b binding protein alpha chain.

6. The method according to claim 1, wherein step (a) comprises at least one of spectrometry such as mass spectrometry, surface enhanced Raman spectroscopy, flow cytometry, ELISA, protein arrays including mass-sensing BioCD protein array, protein micro-arrays, quantum dots based detection, electrochemical immunoassay, gel electrophoresis, 9G DNA technology, nanoparticles including lanthanide chelates such as europium EuNPs and gold nanoparticles, immune-affinity mass spectrometry and immune capture mass spectrometry.

7. The method according to claim 6, wherein step (a) comprises multiple reaction monitoring (MRM) mass spectrometry.

8. The method according to claim 1, wherein step (a) comprises assessing the expression level of the at least one protein by assessing the amount of a fragment or peptide of the at least one protein.

9. The method according to claim 1, wherein step (a) comprises quantifying the expression level of the at least one protein.

10. The method according to claim 1, wherein step (a) comprises quantifying the expression level of the at least one protein relative to the expression level of the at least one protein in a subject without endometriosis.

11. The method according to claim 1, wherein step (a) comprises labelling the at least one protein.

12. The method according to claim 1, wherein the sample comprises a biological sample and/or a sub-sample thereof.

13. The method according to claim 12, wherein the biological sample is a body fluid such as blood, serum, plasma, urine, sweat, tears, saliva, sputum, or any combination or fraction thereof.

14. The method according to claim 1, wherein the sample comprises blood.

15. The method according to claim 1, wherein step (b) comprises comparing the expression level from step (a) with a reference value indicative of endometriosis.

* * * * *